United States Patent [19]

Heckele

[11] 4,076,018
[45] Feb. 28, 1978

[54] ENDOSCOPES

[75] Inventor: Helmut Heckele, Knittlingen, Germany

[73] Assignee: Richard Wolf GmbH, Knittlingen, Germany

[21] Appl. No.: 636,802

[22] Filed: Dec. 1, 1975

[30] Foreign Application Priority Data

Dec. 6, 1974   Germany ..................... 7440701[U]

[51] Int. Cl.² ............................................. A61B 1/06
[52] U.S. Cl. ........................................ 128/6; 350/47;
350/61; 219/219
[58] Field of Search .............. 128/4, 6, 7, 8, 9, 11;
350/253, 64, 61, 96, 46, 47, 54, 175 E; 219/522,
19

[56] References Cited
U.S. PATENT DOCUMENTS

| | | | |
|---|---|---|---|
| 702,048 | 6/1902 | Common | 350/47 |
| 1,791,254 | 2/1931 | Brockdorff | 350/253 |
| 2,171,360 | 8/1939 | Strang | 350/47 |
| 2,585,273 | 2/1952 | Prutzman | 219/19 |
| 2,722,160 | 11/1955 | Prutzman | 350/61 |
| 3,111,570 | 11/1963 | Strang et al. | 219/19 |
| 3,135,004 | 6/1964 | Naigraw | 350/61 X |
| 3,145,249 | 8/1964 | Meltzer | 350/64 |
| 3,297,022 | 1/1967 | Wallace | 128/6 |
| 3,434,775 | 3/1969 | Gosselin | 350/96 |
| 3,495,259 | 2/1970 | Rocholl et al. | 219/522 |
| 3,686,473 | 8/1972 | Shirn | 350/61 X |
| 3,901,220 | 8/1975 | Koyasu | 128/6 |

*Primary Examiner*—Aldrich F. Medbery
*Attorney, Agent, or Firm*—Kinzer, Plyer, Dorn & McEachran

[57] ABSTRACT

A magnifying lens incorporated in an endoscope optical system for viewing an illuminated area to be examined by means of the endoscope is adjustable between end positions in which it lies behind and in front of the focus of the optical system respectively, whereby to enable general examination of said area at a relatively small magnification and a more detailed examination of said area at a relatively higher magnification. A viewing window of an endoscope optical system is heated by an electrical heating conductor to guard against clouding of the viewing window, for example by the breath of a patient.

3 Claims, 5 Drawing Figures

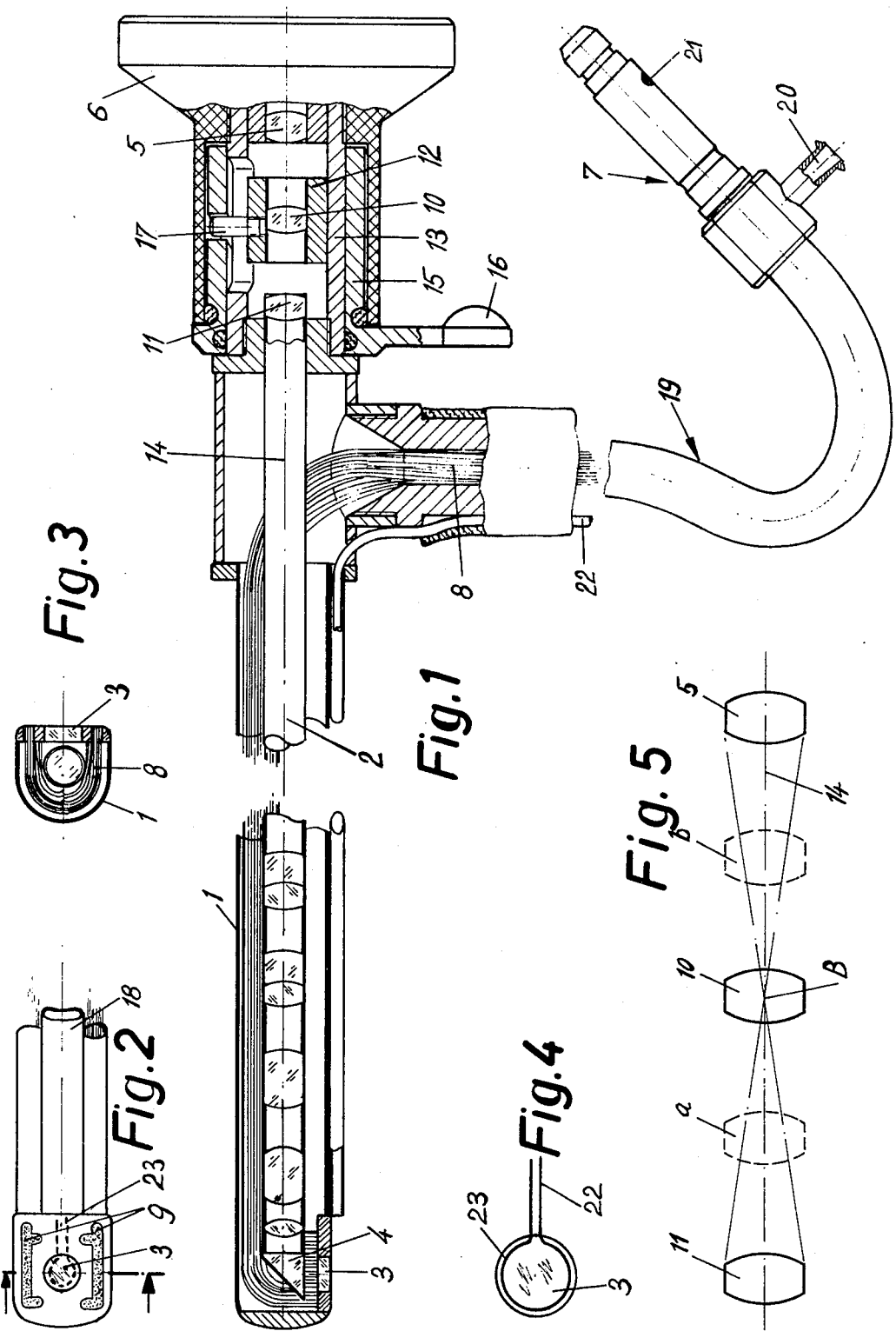

ENDOSCOPES

BACKGROUND OF THE INVENTION

1. Field of the Invention

The invention relates to an endoscope, in particular a laryngoscope and eiphyaryngoscope, comprising a barrel having a light-guide passing therethrough, and an optical system for viewing an area to be examined while under illumination. Such an endoscope will hereinafter be referred to as "of the kind described".

2. Description of the Prior Art

Endoscopes of the kind described are intended, inter alia, to make it easier to observe and examine the larynx and epipharynx, given that the methods of examination previously employed, which involved mirrors, optical systems and the like, called for unusual manual dexterity on the part of the doctor performing the examination, in some cases could not be employed because of anatomical abnormalities, frequently prevented optimum results being achieved, and made it difficult or impossible to make records, which is the case with examination by mirror for example.

SUMMARY OF THE INVENTION

Accordingly, the main object of the present invention is to provide an endoscope, which is particularly suitable for use as a laryngoscope or ehpipharyngoscope, by means of which the larynx and other body cavities can easily be examined, especially in cases where, following a general inspection of the area to be examined, there is to be a detailed inspection as well.

Another object of the present invention is to provide an endoscope of the kind described and having a distal window for the optical system or an exit window for the objective lens in which the window in each case can be kept free of clouding resulting from the condensation of moisture.

To this end, the invention consists in an endoscope of the kind described in which a magnifying lens which can be adjusted between two terminal positions at the proximal end is incorporated in the optical system in such a way that in one terminal position it lies in front of a focus of the optical system and in the other terminal position lies behind this focus.

By this means it becomes possible initially to make a general examination of the area to be inspected, which may be the plane of the vocal cords for example, at a relatively small magnification and thus a large angle of view. When the person performing the examination wishes to examine a detail more closely, he adjusts the lens system in the appropriate direction so that the detail, which may perhaps be something of a pathological nature which has been discovered, is increasingly enlarged as the angle of view becomes smaller. In this way extremely precise examination and inspection become possible and at the same time incorrect diagnosis is largely avoided.

Practical experience has shown, particularly when the mouth and throat regions are being examined, that the patient's breath causes the viewing window or objective plate to become obscured. The result of this is that the standard of the image which is seen suffers because the obscuring layer, being moisture condensation, causes light losses along the optical path of the optical system and, amongst other things, detracts from the quality of the image as a result of optical distortion.

To avoid disadvantages of this nature, the procedure adopted in accordance with a feature of the invention in the case of endorscopes which have a viewing window is to heat the window with an electrical heating conductor which is connected to a source of heating current via a connection at the proximal end of the endoscope.

When condensation may be expected on the window, the heating conductor is supplied with a preferably adjustable heating current in order to bring the temperature of the window, or at least of that face of the window adjacent the area to be examined, to a temperature which is higher than the dew point of the air breathed by the patient. In this way clouding of the objective or viewing window, and the frequent cleaning which would otherwise be necessary, are avoided at the outset.

BRIEF DESCRIPTION OF THE DRAWINGS

FIG. 1 is a partial view in longitudinal section through an embodiment of an endoscope in the form of a laryngoscope and constructed in accordance with the invention, FIG. 2 shows a plan view of the distal end of the endoscope, FIG. 3 shows a section through the barrel of the endoscope in the area occuped by the viewing window, FIG. 4 shows a plan view of the viewing window with a heating wire fitted, and FIG. 5 is a schematic view of one possible arrangement for the magnifying lens.

DESCRIPTION OF THE PREFERRED EMBODIMENT

The instrument shown in FIG. 1 comprises a barrel 1 inside which an optical system made up of lenses is housed in a viewing tube 2. Via a viewing window 3 and a deviating prism 4, the light forming the image passes through the optical system to an eyepiece lens 5, which is followed by a conventional eyepiece 6. The light required to see the image reaches the distal end of the instrument from a light source (not shown), via a connector 7 and fibre light-guide 8. At the distal end of the endoscope the light guide is divided to either side of the window 3 to form two exit surfaces 9 for the light which are ground flat. Instead of being continuous in the way shown, the light-guide 8 could also terminate at the proximal end of the endoscope and the remainder of it connected in a known way to the instrument by means of a coupling.

As can be seen in FIG. 5, a magnifying lens 10 which is axially adjustable lies between the eyepiece lens 5 and the last lens 11 of the optical system, and is so arranged that in one terminal position $a$ it lies in front of the focus B of the optical system in that area and in the other possible terminal position $b$ it lies behind this focus. By virtue of the laws of optics, this means that on the one hand it is possible to select high magnification at a small angle of view to enlarge details and on the other low magnification at a large angle of view for general inspection.

Using a suitable setting mechanism, the magnifying lens 10 may be continuously or discontinuously adjusted as desired in the axial direction, for example by mechanical or motor means, so that the factor of enlargement required in any particular case may be arrived at. A possible way of adjusting the lens mechanically is shown in FIG. 1.

In FIG. 1, the magnifying lens 10 is held in a tubular key member 12 which in turn is guided in the direction of the longitudinal axis 14 of the barrel 1 in a fixed guide tube 13 which is coaxial with it. This assembly is likewise surrounded co-axially by an axially immovable setting or adjusting tube 15 which can be rotated about the axis 14 by means of a setting or adjusting lever 16.

A setting pin 17 projecting from the outer periphery of the tubular member on which the pin is mounted extends through an axial guide opening or slot in the wall of the guide tube 13. The free end of the pin 17 engages in an adjusting groove or slot which is formed in the outer periphery of tubular member 15, whose path, when developed, must contain an axial component. If the path of the adjusting groove, when developed, is an oblique straight line, this means that a relatively small angle of rotation is required to adjust the magnifying lens between its two possible terminal positions. The possibility also exists of the adjusting groove, when considered as developed onto a plane, being of comparatively small inclination at the ends so as to provide a relatively fine adjustment near the possible terminal positions of the lens.

Thus, when setting tube 15 is turned by means of lever 16, lens 10 is adjusted axially in one or other direction, depending on the direction of rotation, for example to bring it to one of the terminal positions *a* and *b* shown in FIG. 5 and to arrive at the factors of magnification which these permit. Alternatively, the pin 17 may be mounted on the tube 15 and the adjusting groove in which the pin engages be in the wall of the tubular member 12.

As already stated other methods of adjusting the magnifying lens may be considered in addition to the purely mechanical one. Thus, instead of the manual method shown, it is for example possible to use a minature geared motor with an appropriate switching device in series. Another method which may be considered is adjusting the magnifying lens from outside by means of a magnetic field. Such a system would have the advantage that no sealing problems would arise, these being known to be particularly critical in endoscopes.

Clouding of the viewing window, which is composed in the conventional manner of glass and may even be formed by the objective lens itself, could be avoided by continuously scavenging the window with air by means of an air supply tube 18 whose free end is directed onto the window. This tube extends, inside or outside the barrel 1 and via a connecting pipe 19, to an air connection 20 on connector 7, to which an air pump, a bottle of pressurised gas or the normal gas supply available in a clinic may be connected as desired.

However, alternatively or in addition, clouding of the window 3 may be prevented with particular advantage by heating the window with an electrical heating conductor which may be connected to a source of heating current via a connection at the proximal end of the endoscope. For this purpose electrical contacts 21 which are isolated from connector 7 may be provided on the connector, these contacts being connected to a heating conductor 23 by means of electrical leads 22 which extend through pipe 19 and barrel 1.

If the window 3 is only to be heated electrically, the air connection 20 and tube 18 may naturally be dispensed with. Another possibility also exists, namely that the electrical contacts for the heating conductor may be incorporated in the connection for cold light so that it is then only necessary to insert the end of the light conducting cable into a modified source of cold light for light, heating current and/or air to be brought simultaneously to the tip of the instrument through appropriate lines.

There are a number of different possible ways of forming and fitting the heating conductor. Thus, the heating conductor may for example be applied to either the inwardly or outwardly directed face of the window 3, or it could be also be embedded in the viewing window by being fused in. FIG. 4 shows an embodiment in which the heating conductor extends at a distance around the centre of window 3 in the form of a loop and is attached to the window. A further possibility is for the viewing window to be held in an annular insulating body with the heating conductor situated on or in this insulating body. There may be advantages in this embodiment in that the heating conductor does not lie directly on the optical path.

A further procedure which might be adopted would be for the heating conductor to cover the viewing window 3 in the form of a thin, transparent layer. For this purpose, the heating conductor could consist of a layer of metal which was vapour-deposited on the window. An electrically conductive lacquer might also be considered. If light losses are found to be too great with these embodiments, the possibility also exists of having the conductive layer cover only part of the viewing window, preferably forming a part-annular area near the circumference of the window.

As FIG. 2 in particular clearly shows, the exit area of light guide 8 is situated in the immediate neighbourhood of viewing window 3. This ensures that the end of the light guide is also situated in the area where temperature is influenced by heating conductor 23 and thus that clouding of the exit faces of the light guide is very largely avoided. The possibility also exists of heating the distal exit faces of the light guide with at least one separately provided electrical heating conductor in order in this way to prevent them from becoming obscured.

Various modifications may be made without departing from the scope of the invention as defined in the appended claims. For example, in place of an endoscopic optical system made up of lenses, it is also possible to use a known optical fibre system in which case a flexible barrel can be used instead of the rigid barrel 1. In this case the proximal end of the optical fibre would have a lens associated with it which in principle would take over the role of lens 11 as the last lens in the optical system, so that in this case too it would be possible for the magnifying lens 10 to lie in front of a focus of the optical system in one terminal position and behind this focus in the other terminal position.

Furthermore, the magnifying lens may be constructed by cementing together a plurality of lens to form a compound lens. Alternatively or additionally, the magnifying or compound lens may have another lens or other lenses associated with it whose functions may be optical correction and the like, which results in there being a group of lenses.

In this specification the term "viewing window" means a separate transparent window or the objective lens of the optical system.

I claim:
 1. An endoscope comprising
  a. a barrel
  b. a light guide passing through said barrel c. an optical system for viewing an illuminated area to be examined, said optical system having a focus,
d. a magnifying lens incorporated in said optical system and
e. means for selectively varying the magnification of the object to be viewed, thereby to enable the object to be viewed at one enlargement and view angle on the one hand and a different enlargement and view angle on the other hand, said means comprising a setting mechanism coupled to said magnifying lens for effecting axial displacement of said magnifying lens between two positions in which said magnifying lens lies in front of and behind said focus respectively.

2. An endoscope according to claim 1, wherein said means for adjusting said magnifying lens comprises a setting mechanism which is mechanically coupled to said magnifying lens and which includes mechanical means for effecting axial displacement of said magnifying lens to set the magnification factor of said magnifying lens.

3. An endoscope according to claim 1, wherein said means for adjusting said magnifying lens comprises a tubular mounting member for said magnifying lens and defining a light passage in which said magnifying lens is mounted, means for moving said mounting member axially of said barrel and a tubular guide member which encircles said mounting member and which is fixed with respect thereto, said guide member defining an axial guide slot in which said mounting member slides to prevent rotation of said mounting member whilst permitting axial movement thereof and which has end portions defining said two end positions respectively of said magnifying lens, said means for moving said mounting member axially including a rotatable tubular member encircling said fixed guide member and a key projecting from one of said mounting and rotatable members through said slot in said guide member, one of said rotatable tubular and mounting members defining a key-way which is inclined with respect to the axis of the barrel and in which said key engages, and means for rotating said rotatable tubular member, and wherein said optical system terminates in a viewing window at a distal end region of said endoscope, means are provided for heating said viewing window, including an electrical heating conductor, electrical connecting wires passing through said barrel and a connection at a proximal end region of said endoscope connected to said connecting lines, for connecting said electrical heating conductor to a source of electric current.

* * * * *